United States Patent [19]

Bailey

[11] 4,206,768
[45] Jun. 10, 1980

[54] SYRINGE DEVICE WITH MEANS FOR SELECTIVELY ISOLATING A BLOOD SAMPLE AFTER REMOVAL OF CONTAMINATES

[75] Inventor: Donald L. Bailey, Thornton, Colo.

[73] Assignee: Marquest Medical Products, Inc., Englewood, Colo.

[21] Appl. No.: 952,994

[22] Filed: Oct. 20, 1978

[51] Int. Cl.² ............................................. A61B 5/14
[52] U.S. Cl. ............................ 128/763; 128/218 PA
[58] Field of Search ............ 128/763, 765, 766, 218 P, 128/218 PA, 238, 218 S, 218 R, 234; 222/386

[56] References Cited

U.S. PATENT DOCUMENTS

| | | | |
|---|---|---|---|
| 3,943,917 | 3/1976 | Johansen | 128/763 |
| 3,985,122 | 10/1976 | Topham | 128/765 |
| 4,020,831 | 5/1977 | Adler | 128/765 |

FOREIGN PATENT DOCUMENTS 1566602 12/1967 Fed. Rep. of Germany ....... 128/218 P

*Primary Examiner*—Kyle L. Howell
*Attorney, Agent, or Firm*—Gary M. Polumbus

[57] ABSTRACT

A syringe is disclosed for taking blood samples which includes a tubular body, a plunger, a sealing member and a needle. The plunger and sealing member in combination are slideably received in the tubular body with the plunger receiving the sealing member for rotational movement about its longitudinal axis. The sealing member has two longitudinally spaced circumferential sealing locations with a cylindrical space between the sealing locations. Two closeable openings through each seal location are established in the sealing member at 180° opposition to each other by a thread extending across each seal. The thread is attached to the plunger so that after blood passes through the seal nearest the needle end of the syringe, the plunger can be rotated to remove the thread from both seal locations thereby sealing the blood sample in the tubular body after all gases have been purged from the tubular body.

8 Claims, 12 Drawing Figures

SYRINGE DEVICE WITH MEANS FOR SELECTIVELY ISOLATING A BLOOD SAMPLE AFTER REMOVAL OF CONTAMINATES

BACKGROUND OF THE INVENTION

In blood gas analysis, it is important that air or other gaseous material not be allowed to contaminate the blood as these contaminates distort the results of the gas analysis. To compound this problem, most prior art syringes adapted to withdraw blood samples from donors are normally preconditioned by the addition of a heparin solution to provide an anticoagulant for the blood. The heparin solution is typically very dilute with the heparin concentration being approximately 1000 units per milliliter and the diluent being made up of alcohol, water, and other materials which can distort the gas analysis of the blood.

It is desirable in taking blood samples for gas analysis to isolate the blood from extraneous gaseous materials and from the diluent of the heparin solution while leaving the heparin itself to prevent coagulation of the blood.

Accordingly, it is an object of the present invention to provide a new and improved method of and syringe for taking blood samples which prevents contamination by extraneous gases which are inherently present in a syringe body or in the diluent of a heparin solution which is added to a syringe prior to use.

SUMMARY OF THE INVENTION

The syringe of the present invention includes a main tubular body which slideably receives a sealing member and plunger in combination. The leading end of the tubular body includes an opening in communication with a cylindrical end element adapted to receive a hypodermic needle or the like through which blood can pass into the chamber defined by the tubular body. The interior chamber of the tubular body is selectively closed at the end opposite the needle by a sealing member of generally cylindrical shape. Each end of the sealing member is of an enlarged diameter so that contact sufficient to create a seal exists between the sealing member at each end and the syringe body. The sealing member is moved longitudinally along the syringe body, if necessary, by the plunger. The plunger also fits inside the sealing member in such a manner that the plunger may be rotated about its longitudinal axis relative to the sealing member.

A thread connected to the plunger is positioned, prior to use, so that the seal between the sealing member and the syringe body is interrupted by the presence of the thread allowing gaseous material to be flushed from the interior chamber by a blood sample flowing into the chamber. The thread can be removed from its position interrupting the seal by rotation of the plunger after blood is observed breaching the seal, leaving the interior chamber of the syringe full of blood and purged of gaseous material. Also, the walls of the passage admitting blood into the interior chamber of the syringe may be coated with an anticoagulant prior to drawing the blood sample to prevent the blood from coagulating in the syringe and to avoid the use of liquid anticoagulant which also contains diluent components which can distort the blood gas analysis.

DESCRIPTION OF THE PREFERRED EMBODIMENT

Figure 1:
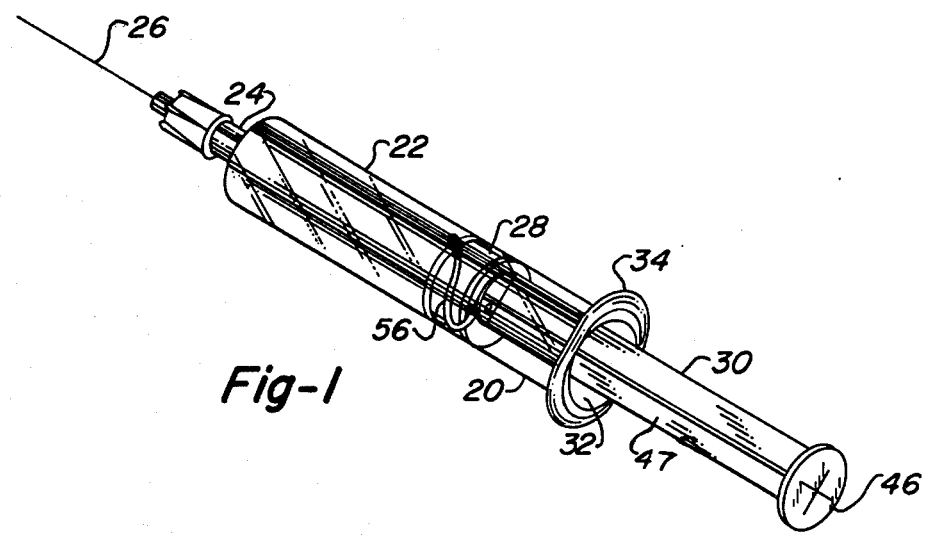
FIG. 1 is a perspective view of the syringe of the present invention.
Figure 2:
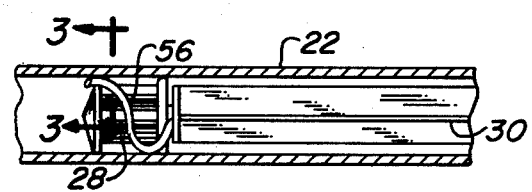
FIG. 2 is a side view of the sealing member and plunger showing the position of the thread prior to rotation of the plunger.
Figure 3:
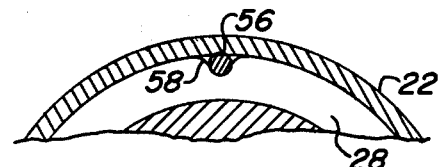
FIG. 3 is an enlarged section taken along line 3—3 of FIG. 2.
Figure 4:
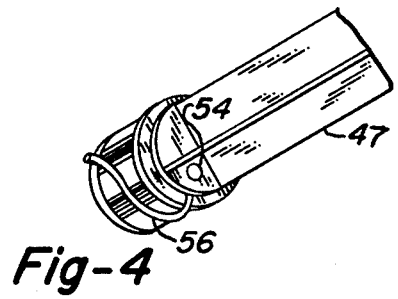
FIG. 4 is a perspective view of the sealing member and plunger with the thread positioned in a seal breaking position.
Figure 5:
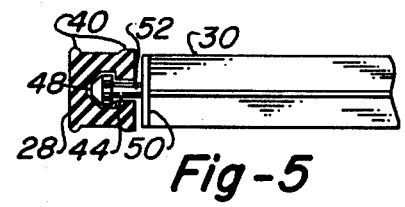
FIG. 5 is a longitudinal section illustrating the connection of the sealing member and plunger.

A preferred form of the syringe 20 of the present invention includes a transparent or translucent main tubular body 22 of circular transverse cross section having an end fitting 24 protruding from one end to which a hypodermic needle 26 is frictionally connected by the needle connector 23, in an hermetically sealed relation. A sealing member 28 is rotatably mounted on a plunger 30 in a manner such that the sealing member can slide along the interior of the main tubular body.

The main tubular body 22 has an open circular tubular body 22 has an end member 36 with a central, longitudinal, forwardly extending neck 24. The neck 24 is hollow and communicates with the interior chamber 38 of the syringe body 22.

The sealing member 28 is constructed of a material having elastic and resilient properties such as rubber. In its undeformed shape, the sealing member 28 is generally cylindrical in shape with a circular lip 40 at either end. The lips 40 are of sufficient diameter to contact the interior surface of the syringe body 22 and form a hermetic seal therewith. A cylindrical void space 42 is defined between the sealing member body, the lips 40 and the internal wall of the main tubular body 22 for a purpose to be described later. The sealing member 28 includes a recessed area 44 in its trailing end of T-shaped cross section adapted to rotatably receive and hold one end of the plunger 30.

The plunger 30 is an elongated rod including a disc 46 on the trailing end, an intermediate body portion 47 of X-shaped cross section, and a disc 50 near the leading end. A small diameter pin 52 forms a reduced diameter portion of the rod body 47 and a relatively small disc 48 is disposed on the leading end of the pin 52. The pin 52 and disc 48 are shaped to fit rotatably within the recess 44 of the sealing member 28.

The disc 50 of the plunger 30 has a bore 54 through it to which a thread 56 is tied. The thread 50 is of a length sufficient to be tied off at the bore 54 and extend across both sealing lips 40 of the sealing member 28. The thread 56 is made of flexible material, such as nylon or cotton and has a diameter sufficient to form a breach or space 58 between the sealing member 28 and the syringe body 22 when the thread 56 is extended across the lips 40 of the sealing member 28.

As mentioned previously, the plunger 30 is rotatably received within the sealing member 28. The disc 48 and pin 52 combined with the mating shape of the recess 44 allows the sealing member 28 to be moved axially within the syringe body 22 by the plunger 30. The circular configuration of the disc and the mating recess permits rotational movement of the plunger relative to the sealing member for a purpose which will become more clear later.

The hypodermic needle 26 is connected to the syringe 20 at the end fitting 24 in a manner well known in the art. The entire syringe and parts thereof are made of sterilizable materials so that they can be sterilized before use. Preferably the materials are so inexpensive that the syringe can be disposed of after use.

Typically, the syringe is prepared for use by drawing a diluent of anticoagulant 60, such as heparin, through the bore 24 and into the interior chamber 38 of the tubular body of the syringe 20. The solution of anticoagulant is allowed to evaporate leaving dried anticoagulant as a precipitated coating in the interior chamber of the tubular syringe body. The process can be quickened by heating the syringe body and the anticoagulant after the anticoagulant has been drawn into the interior chamber. The syringe body is then attached to the hypodermic needle.

The thread 56 is attached to the plunger 30 by extending it through the bore 54 and knotting the corresponding end of the thread. The thread is extended completely across the sealing member 28, slightly indenting body lips 40 at breached locations identified by the numeral 58. In the preferred embodiment the thread crosses each of the lips 40 at a 180° displacement relative to the other lip crossing point for a reason to be explaned later. The plunger, sealing member and thread 56 are slideably insertable into the syringe body 22 through the open circular end 32. The plunger is used to position the sealing member at a point along the tubular body corresponding to the volume of blood sample desired.

In the operation of the syringe, the hypodermic needle is inserted into the artery of the donor patient where the blood pressure will force the blood through the needle into the interior chamber 38 of the syringe body 22. The individual taking the sample should orient the syringe so that the breach 58 in the seal lip 40 nearest the needle of the syringe body is disposed so as to be at the furthest distance possible from the rising level of the blood as it enters the interior chamber. The sealing member 28 thus acts as a dam and the breach created by the thread 56 serves as a vent and, ultimately after the chamber is filled with blood, it serves as a spillway through which the blood can pass into the void space 42. It will be appreciated that as the blood fills the interior chamber, the chamber is purged of all gaseous materials that might contaminate the blood sample.

Figure 6:
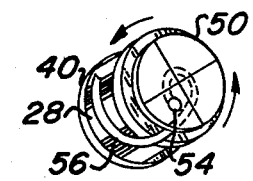
FIG. 6 is a perspective view of the sealing member and plunger with the thread having been moved by rotation of the plunger to restore one sealing interface between the sealing member and syringe body.
Figure 7:
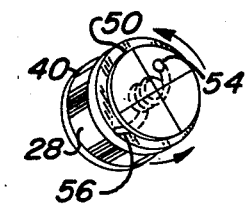
FIG. 7 is a perspective view of the sealing member and plunger with the thread having been moved to restore both sealing interfaces between the sealing member and syringe body.
Figure 8:
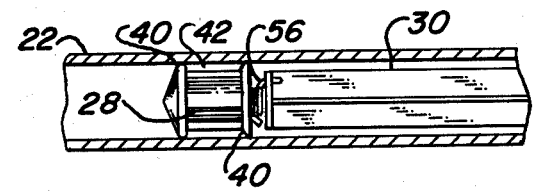
FIG. 8 is a side view of the sealing member and plunger showing the position of the nylon thread after the plunger has been rotated to restore both seals.
Figure 9:
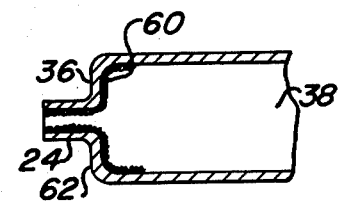
FIG. 9 is a fragmentary longitudinal section of the syringe body, at the end connected to the hypodermic needle indicating the areas to which anticoagulant is applied.
Figure 10:
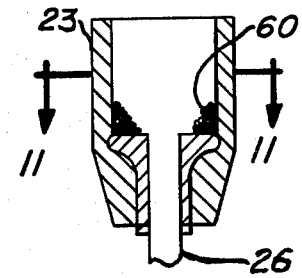
FIG. 10 is an enlarged fragmentary longitudinal section of the needle, indicating the area to which anticoagulant is applied.
Figure 11:
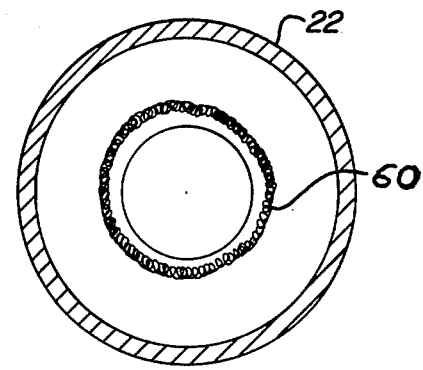
FIG. 11 is a section taken along line 11—11 of FIG. 10.
Figure 12:
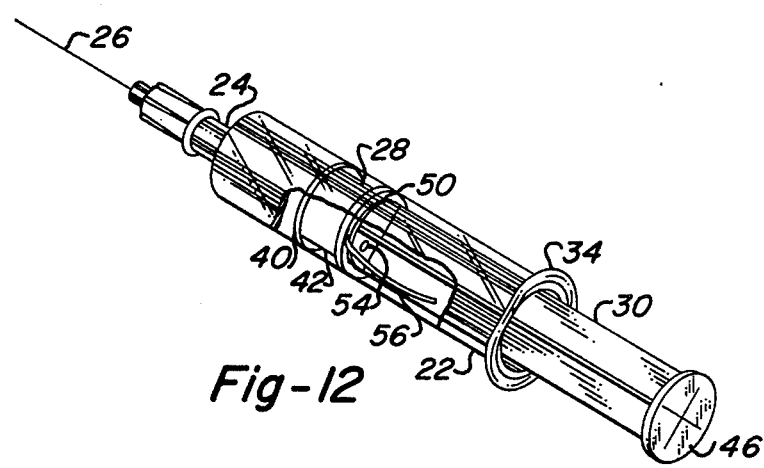
FIG. 12 is a perspective view of the syringe of the present invention with the thread not being used to break the seal between the sealing member and the syringe body.

As the blood reaches the breach point 58 and crosses the first lip 40 into the void space 42, the plunger 30 is rotated as illustrated in FIG. 6 so as to wind the thread 56 about the plunger thus pulling the thread past the forwardmost sealing lip establishing a complete seal at that location. Continued rotation of the plunger as illustrated in FIGS. 7 and 8 will pull the thread past the second lip of the sealing member thus establishing a complete seal at that location to trap the blood that flowed into the void space and thus prevents leakage of any blood from the syringe.

When the syringe 20 is used in a donor having an extremely low blood pressure, such pressure being insufficient to completely fill the interior chamber 38 of the syringe in a short period of time, the sealing member is pre-set at a level of approximately 0.1 cc to 0.2 cc and an amount of blood sufficient to fill the reduced volume interior chamber is allowed to flow into the chamber. Once blood is observed in the void 42 between the lips 40 of the sealing member, the plunger is rotated to establish a seal, as has previously been described in operations relative to individuals of higher blood pressure. The sealing member is then withdrawn to create a low pressure zone to draw more blood into the interior chamber until the desired volume is in the syringe. Again, it will be appreciated that the blood sample obtained will be free of contaminants so that blood gas analysis which may be performed on the sample will be undistorted.

It will be understood that changes may be made in the details of construction, arrangement and operation without departing from the spirit of the invention, especially as defined in the following claims.

What is claimed is:

1. A syringe device for drawing blood samples comprising
    a tubular body having an interior surface defining an elongated interior chamber, said tubular body having one open end and an end member at the opposite end, said end member having a bore therethrough defining means for connection to a hypodermic needle;
    a plunger means slideably positioned within said tubular body;
    a sealing member operatively connected to said plunger means including resilient means capable of establishing an hermetic seal with said interior surface,
    seal interrupting means attached to said plunger adapted to interrupt said hermetic seal; and
    means for moving said seal interrupting means to restore the hermetic seal and thereby prevent fluid flow past said sealing member.

2. The syringe device of claim 1 wherein said sealing member has a generally cylindrical body with circumferential lips at either end, said lips adapted to maintain contact with the interior surface of the tubular body.

3. The syringe device of claim 1 wherein said means for moving said seal interrupting means consists of a rotatable connection between the plunger means and the sealing member.

4. The syringe device of claim 3 wherein the plunger means includes a circular disc connected to an axially extending pin with said disc being rotatably embedded within said sealing member.

5. The syringe device of claim 2 wherein the seal interrupting means comprises a flexible thread adapted to be extended across the lips of said sealing member to deform said lips and thereby form a breach in the lips to allow fluid flow past said lips.

6. The syringe device of claim 5 wherein said seal interrupting means crosses one of said lips at a 180° displacement from the crossing of the other of said lips.

7. The syringe device in claim 2 wherein the sealing member, including the lips thereon and the interior surface of the tubular body define a space into which blood can flow when said interior chamber is full of blood.

8. A syringe device for drawing blood samples comprising:

a tubular body having an interior surface defining an elongated interior chamber, said tubular body having an open end at one end thereof in communication with said interior chamber and an end member at the opposite end of said interior chamber, said end member having an opening therethrough defining means for connection to a hypodermic needle, said tubular body also having a radially extending annular flange around the open end thereof;

a plunger means slideably positioned within said tubular body having a rod-like body defining a handle extending axially out of the open end of said tubular body, two axially spaced circular discs on said rod-like body near the end opposite the handle, said discs being separated by reduced diameter portion of said rod-like body;

a resilient generally cylindrical sealing member having one of said discs rotatably embedded therein so as to be rotatably connected to said plunger means, said sealing member having annular lips at either end which contact the interior surface of the tubular body and define a void therebetween;

seal interruption and seal restoration means including a flexible thread operably connected to the other of said discs on the plunger and adapted to extend across both lips of the sealing member thereby forming a breach at each lip through which fluid can pass, said thread adapted to be wound onto the plunger when the plunger is rotated thereby allowing the sealing member lips to sealingly contact the interior surface of the tubular body and form an hermetic seal therewith.

* * * * *